United States Patent
Chattopadhyay et al.

(10) Patent No.: US 6,365,757 B1
(45) Date of Patent: Apr. 2, 2002

(54) PROCESS FOR THE PRODUCTION OF A COMPOUND (+) CATECHIN PENTA ACETATE USEFUL AS A PRECURSOR FOR THE PRODUCTION OF (+) CATECHIN

(75) Inventors: Sunil Kumar Chattopadhyay; Suchitra Banerjee; Shipra Agarwal; Koneni Venkata Sashidhara; Vinayak Tripathi; Arun Kumar Kukreja; Sushil Kumar; Manish Kulshrestha; Ram Prakash Sharma; Vijay Kumar Mehta, all of Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/535,767

(22) Filed: Mar. 28, 2000

(51) Int. Cl.$^7$ ............................................. C07D 311/04
(52) U.S. Cl. ..................................................... 549/403
(58) Field of Search ........................................ 549/403

(56) References Cited

U.S. PATENT DOCUMENTS 4,906,656 A 3/1990 Laks ........................... 514/456

OTHER PUBLICATIONS

Cahttopadhyay, et al., 1999, National Institute of Science Comm., 38B(2), 246–247.*
Sigma Plant Cell Culture Catalogue, 1991–1992, pp. 7–11.
S. Banerjee et al., "Taxanes from in vitro cultures of the himalayan yew taxus wallachiana," Medical vol. 62, pp. 333–335, 1996.
F. Trotin et al., "Flavanol production of fagopyrum esculetum hairy and normal root cultures," Phytochemistry, vol. 32, No. 4, pp. 929–931, 1993.
Kahn Ono et al., "Catechin production in cultured poygonum hydropiper cells," Phytochemistry, vol. 49, No. 7, pp. 1935–1938, 1998.
T. Bahorun et al., "Comparative polyphenolic productions in crataegus monegyna callus cultures," Phytochemistry, vol. 3y7, No. 5, pp. 1273–1276, 1994.

Y. Moumou et al., "Catechin production by callus cultures of *Fogopyrum esculentum*", Phytochemistry, vol. 31, No. 4, pp. 1239–1241, 1992.
Mondher Jaziri et al., "Taxus sp. Cell, tissue and organ cultures as alternative sources for taxoids production: a literature survey," Plant Cell, Tissue and Organ Culture 46:59–75, 1996.
Eckhard Wollenweber et al., "Occurrence and distribution of free flavonoid aglycones in plants," Phytochemistry, vol. 20, No. 5, pp. 869–932, 1981.
S. Jha et al., "Improved Taxol Yield in Cell Suspension Culture of Taxus wallichiana (Himalayan Yew)," Plant Medica, vol. 64, pp. 270–272, 1998.
Khoon–Huat law et al., "Production of (–) Epicatechin by Uncaria Elliptica Callus Cultures," Phytochemistry, vol. 28, No. 4, pp. 1099–1100, 1989.
Cahttopadhyay, et al., 1999, National Institute of Science Comm., 38B(2), 246–247.

* cited by examiner

*Primary Examiner*—Deborah C. Lambkin
*Assistant Examiner*—Andrea M. D'Souza
(74) *Attorney, Agent, or Firm*—Jenkens & Gilchrist

(57) ABSTRACT

This invention relates to a process for the production of a compound (+) catechin penta acetate of formula I from *Taxus wallichiana* tissue cultures which comprises : (a) inoculation of explants on different media compositions supplemented with combinations of auxins (1–5 mg/l) and cytokinins (0.1–1.0 mg/l); (b) incubation of the cultures under continuous light or dark conditions for 4–6 weeks for callus cultures followed by subculturing at 4–6 weeks intervals; (c) harvesting of the calli at different growth phases ranging from 12–36 months; (d) extraction of fresh pulverized calli with polar solvents at room temperature; (e) evaporating the solvent to give a residue; and partitioning of the residue between water and chlorinated solvents and evaporating the solvent to a semisolid mass; (f) subjecting the resultant mass to column chromatography over suitable adsorbent and (g) eluting with organic solvent/mixtures of organic solvents to get (+) catechin penta acetate.

13 Claims, No Drawings

PROCESS FOR THE PRODUCTION OF A COMPOUND (+) CATECHIN PENTA ACETATE USEFUL AS A PRECURSOR FOR THE PRODUCTION OF (+) CATECHIN

FIELD

This invention relates to a process for the production of compound (+) catechin penta acetate useful as a precursor for the production of (+) catechin. More particularly, this invention relates to a process for the production of (+) catechin penta acetate of formula (1) from *Taxus wallichiana* tissue cultures which is useful as a precursor for the production of (+) catechin of formula (2).

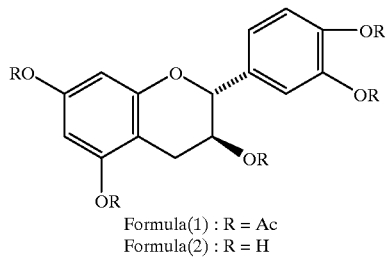

Formula(1) : R = Ac
Formula(2) : R = H (+) catechin peta acetate of formula (1) can be prepared only from (+) catechin of formula (2) through acetylation. Therefore, the only source to get (+) catechin penta acetate consists of two processes—first to isolate (+) catechin and then to convert it into (+) catechin penta acetate through acetylation. However, in this invention, the precursor (+) catechin penta acetate can be directly obtained from the cell cultures of *Taxus wallichiana* following the process of the process of the present invention. Moreover, (+) catechin of formula (2) is a polyphenolic compound and is susceptible to aerial oxidation and forms mixture of compounds on exposure to air. However, (+) catechin penta acetate of formula (1) is a stable molecule and can withstand aerial oxidation. Thus, it has a high self life and can be useful as a precursor for the production of (+) catechin.

BACKGROUND

In recent years, different Taxus species have attracted world wide attention due to the presence of taxol or its analogues in the bark or needles of the trees. Taxol, a highly oxygenated diterpenoid molecule and a potent anticancer drug was first isolated from the stem bark of *Texus brevifolia*. Thereafter, it ahas also been isolated from other Taxus species including *T. wallichiana*.

Catechins, the basic structural unit of condensed tannins, belong to flavan-3-ol derivatives and are found in a wide variety of plant sources such as vegetables, herbs and teas (Phytochem (1981) 20:869). Considerable interest have been expressed regarding the various pharmacological functions of catechins, which have been proved to be antibacterial, antiviral, antitumour, antioxidant and radical scavengers (Phytochem (1998) 49:2379–82).

The direct manipulation of plant cell and tissue culture systems has resulted in an enhanced production of various secondary metabolites. In vitro production of catechins, mainly (−) epicatechin-3-O-gallate accompanied by (+) catechin and (−) epicatechin have been reported in *Fagophyrum esculentum calli* and hairy root cultures (Phytochem (1992) 3 1:1239–1241; Phytochem (1993) 32:929), suspension cultures of *Camellia sinensis* (Chayekexue (1995) 15:111–116) and *Vitis vinifera* (Biotech Lett. (1996) 659–662). *Crataegus monogyna* (Phytochem (1994) 37:1273), *Uncaria elliptica* (Phytochem (1998) 28:1099–1100) and *Polygonum hydropiper* (Phytochem (1998) 49:1935–39).

In a prior art process, (+) catechin was isolated from the cell cultures of *T. wallichiana* with a yield of 0.3%, which comprises inoculation of explants on different media compositions supplemented with combinations of auxins (1–5 mg/l) and cytokinins (0.1–1.0 mg/l), incubation of the cultures under continuous light or dark conditions for 4–6 weeks for callus initiation followed by subculturing at 4–6 weeks intervals, extraction of fresh pulverized calli with polar solvents at room temperature, evaporating the polar solvent to give a residue, and treatment of the residue with a chlorinated solvent and isolation of (+) catechin by filtration (SK Chattopadhyay et al. Indian Patent Application No. 215/DEL/2000, applicants Ref. No. NF364/99).

Several approaches have been used for the establishment of in vitro cultures of various Taxus species (Plant Cell, Tissue and Organ Cult. (1996) 46:59–75). Different explants and various basal media have been used for initiation and maintenance of Taxus callus and cell suspension cultures. The culture media are frequently supplemented with organic substances, such as casein hydrolysate, polyvinylpyrrolidone, ascorbic acid and others. Several growth regulators are used for stimulation of cell proliferation.

*Taxus wallichiana*, known as Himalayan yew is available in India. Suspension and callus cultures of *T. wallichiana* are found capable of producing taxol (Planta Med. (1998) 64:270–72) and some important taxanes, namely 2-deacetoxy-taxinine J and 2-deacetoxy autrospicatin (Planta Med. (1996) 62:333–35). We have been screening different callus lines of *T. wallichiana* induced from different explants of tress collected from different geographical regions of India. The protocol standardized for in vitro callus production is dependent on media composition (viz. Murashinge and Skoog's Gamborg's, White's, Nitsch and Nitsch's), hormonal regime combinations of different concentrations of cytokinins and auxins, (such as 6-benzyl aminopurine, TDZ, 2-ip, Kinetin, 6-methylamino purine, Zeatin with NAA, IAA, IBA, 2,4-D, 2,4-T, Picloram), explant source (preferably from needles, twigs, stems devoid of needles and seeds) and culture conditions (light dark conditions).

The callus line developed from a specific explants on different media compositions having definite hormonal combinations resulted in the production of a compound. The compound, having a molecular formula $C_{25}H_{24}O_{11}$, mp 131–132° C., was isolated as a crystalline solid with a yield of 0.05%. The compound has been characterized as (+) catechin penta acetate.

The (+) catechin penta acetate is a very important precursor for the synthesis of catechin which in turn can be converted into its other biologically active derivatives, eg. gallocatechin, epigallocatechin and epigallocatechin-3-o-gallate.

There has not been any process reported in the literature for direct isolation of (+) catechin penta acetate either from higher plants, microbes or from cell cultures of plants.

Thus, the drawbacks of the previous processes for the preparation of (+) catechin penta acetate are as under:

These processes require isolation of (+) catechin and the convertion thereof to catechin penta acetate through acetylation process.

(+) catechin can not be preserved for a longer period of time due to its instability towards aerial oxidation.

However, (+) catechin penta acetate can be preserved without its decomposition for a longer period of time and it easily can be converted into (+) catechin with a quantitative yield.

OBJECTS

Thus the main object of the present invention is to provide a process for in vitro production of a compound (+) catechin penta acetate of formula 1 from *T. wallichina* tissue cultures.

Another object is to provide a process for isolation of (+) catechin penta acetate from cell cultures of *T. wallichiana*.

Yet another object is to provide a process for the production of a stable precursor (+) catechin penta acetate from *T. wallichiana* tissue cultures for the production of (+) catechin.

Still another object is to provide a process for the production of (+) catechin penta acetate from the cell cultures of *T. wallichiana* which can then be converted into (+) catechin quantitatively.

SUMMARY

The present invention consisting of the in vitro production of (+) catechin penta acetate from *T. wallichiana* constitutes the first ever report of production of (+) catechin penta acetate in the genus Taxus.

In contrast to prior art processes for the production of the precursor (+) catechin penta acetate, which comprises, first isolation of the (+) catechin (which is susceptible to aerial oxidation and polymerization) and then to convert it into catechin penta acetate, this invention provides a process for the direct production of a stable precursor (+) catechin penta acetate in the cell cultures of *T. wallichiana*. Also, this stable precursor (+) catechin penta acetate can be converted into (+) catechin quantitatively.

Thus, the novelty of the present invention is that it provides a process for the in vivo production of a stable precursor (+) catechin penta acetate in the cell cultures of *T. wallichiana*, which can be converted into (+) catechin quantitatively.

DETAILED DESCRIPTION

Accordingly the present invention relates to a process for the production of a compound (+) catechin penta acetate of formula I from *T. wallichiana* tissue cultures which comprises:

(a) inoculation of explants on different media compositions supplemented with combinations of auxins (1–5 mg/l) and cytokinins (0.1–1.0 mg/l);

(b) incubation of the cultures under continuous light or dark conditions for 4–6 weeks for callus initiation followed by subculturing at 4–6 weeks intervals;

(c) harvesting the calli at different growth phases ranging from 12 to 36 months;

(d) extraction of fresh pulverized calli with polar solvents at room temperature;

(e) evaporating the polar solvent to give a residue; and partitioning of the residue between water and chlorinated solvent and evaporating the solvent to semi-solid mass;

(f) subjecting the resultant mass to column chromatography over suitable adsorbents and (g) eluting with organic solvent/mixtures of organic solvent to get catechin penta acetate.

In an embodiment of the present invention the explants for induction of callus may be selected from needles, twigs, stem devoid of needles and seeds.

In another embodiment of the present invention the culture media for callus induction and multiplication may be selected from Murashige and Skoog; (1962) (MS) medium, containing the following (in mg/l)- $NH_4NO_3$ (1,650), $KNO_3$ (1,900), $CaCl_2.2H_2O$ (400), $MgSO_4.7H_2O$ (370), $KH_2PO_4$ (170), $Na_2EDTA.2H_2O$ (7.2), $FeSO_4.7H2O$ (27.8), $MnSO_4.4H_2O$ (22.3), $ZnSO_4.7H_2O$ (8.6), $H_3BO_3$ (6.2), KI (0.83), $Na_2MoO_4.2H_2O$ (0.25), $CuSO_4.5H_2O$ (0.025), $CoCl_2.6H_2O$ (0.025), Glycine (2.0), Nicotinic acid (0.5), Pyridoxine HCL (0.5), Thiamine HCl (0.1); Gamborg's (1968) (B5) medium, containing the following (in mg/l)- $KNO_3$ (3,000), $(NH_4)_2SO_4$ (134), $MgSO_4.7H_2O$ (500), $CaCl_2.2H_2O$ (150), $NaH_2PO_4.H_2O$ (150), $MnSO_4.H_2O$ (10.0), KI (0.75), $H_3BO_3$ (3.0), $ZnSO_4.7H_2O$ (2.0), $CuSO_4$ (0.025), $NaMoO_4.2H_2O$ (0.25), $CoCl_2.6H_2O$ (0.25), $Na_2EDTA.2H_2O$ (37.2), $FeSO_4.7H_2O$ (27.8); White's (1963) medium, consisting of the following (in mg/l)- $Ca(NO_3)_2$ (142.0), $KNO_3$ (81.0), $MgSO_4.7H_2O$ (70.0), KCl (65.0), $KH_2PO_4$ (12.0), $Fe(SO_4)_3$ (2.46) and Nitsch and Nitsch; (1969) medium, containing the following (in mg/l)- $NH_4NO_3$ (20.0), $KNO_3$ (950), $H_3BO_3$ (10.0), $KH_2PO_4$ (68.0), $Na_2MoO_4.2H_2O$ (0.143), $CaCl_2$ (41.5), $MgSO_4.7H_2O$ (185), $MnSO_4.4H_2O$ (15.0), $ZnSO_4.H_2O$ (10.0), $CuSO_4$ (0.14), $FeSO_4$ (111.4), $Na_2EDTA$ (149), Biotin (0.05), Glycine (2.0), Nicotinic acid (5.0), Pyridoxine HCl (0.5), Thiamine HCl (0.5), Folic acid (5.0).

In yet another embodiment, the auxins may be selected from indole acetic acid (IAA), napthelene acetic acid (NAA), indole butyric acid (IBA), 2,4-dichlorophenoxy acetic acid (2,4-D), 2,4,6-trichlorophenoxy acetic acid (2,4-T) and picloram within the following range (0.2–20 mg/l).

In still another embodiment, the cytokinins may be selected from 6-benzyl amino purine (BAP), 6-methyl aminopurine (MAP), kinetin (Kn), zeatin, thiadiazuron (TDZ) and 2-isopentenyl amino purine (2-ip) within the following range (0.02–2 mg/l).

In still another embodiment, the cultures may be incubated under continuous light of 300—300 lux or under continuous dark conditions.

In still another embodiment, harvesting time get maximum product may be from twenty four to thirty six months.

In still another embodiment of the present invention, the polar solvents may be selected from methanol, ethanol, propanol and butanol.

In still another embodiment, the ratio of auxin and cytokinin used ranges between 5 to 20:1.

In still another embodiment, the medium may be supplemented with casein hydrolysate ranging between 100 to 400 mg/l.

In still another embodiment, ascorbic acid used ranges between 10–50 mg/l.

In still another embodiment, the chlorinated solvents used for partitioning may be selected from chloroform, dichloromethane.

In still another embodiment, the adsorbents used for column chromatography for isolating catechin penta acetate may be selected from silica gel, alumina and florosil.

In still another embodiment, the organic solvent, mixtures of organic solvents used for eluting the column may be selected from ethyl acetate, chloroform, dichloromethane, hexane-ethyl acetate mixtures, pet.ether-ethyl acetate mixtures, hexane-chloroform mixtures, pet. ether-chloroform mixtures.

Repeated experimentations have proved that use of particular explants and specific ratio of auxins and cytokinins are the critical factors for in vitro expression of (+) catechin penta acetate production.

The invention is described in detail in the examples given below which are provided to illustrate the invention and therefore should not be construed to limit the scope of the invention.

EXAMPLE-1

Needle explants of mature trees of *T. wallichiana* were collected from geographical regions of India and callus cultures were initiated on Murashige and Skoog's (MS) basal medium supplemented with 2,4-D (5 mg/l), Kinetin (0.25 mg/l), ascorbic acid (40 mg/l), sucrose (3%) and agar (0.8%). The cultures were maintained at 25±2° C. under continuous light condition (3000 lux). After initiation, the callus was maintained on the same medium with subculturing at every 4 weeks. The calli were harvested at different growth phases and extracted with methanol (5 g/20 ml). The methanol extract was concentrated under reduced pressure to a semisolid residue. The residue was treated with chloroform with stirring to obatin solids. The solids were filtered to give (+) catechin as amorphorus solid yield (0.3%).

EXAMPLE 2

Needle explants of mature trees of *T. wallichiana* were collected from different geographical regions of India, and callus cultures were initiated on Murashinge and Skoog's (MS) basal medium supplemented with 2,4-D (5 mg/l), kinetin (0.25 m/l), ascorbic acid (40 mg/l), sucrose (3%), agar (0.8%). The cultures were maintained at 25±2° C. under continuous light condition (3000 lux).

After initiation, the callus maintained on the same medium with sub-culturing at every 4 weeks. The calli were harvested at different growth phases and extracted with methanol (5 g/20 ml). The methanol extract was concentrated under reduced pressure to a semisolid residue. The residue was treated with water and extracted with chloroform.

The chloroform extract was column chromatographed over silica gel (60–120 mesh): The column was first eluted with pet. ether and then with 10% ethyl acetate in pet. Ether. The eluant of the latter fraction on concentration gave catechin penta acetate (yield 0.05%).

EXAMPLE 3

Young twigs were collected from mature trees of *Taxus wallichiana* and inoculated on Gamborg's (B5 medium supplemented with 2,4-D (2 mg/1), picloram (3 mg/l), Kn (0.25 mg/l), casein hydrolysate (250 mg/l), sucrose (30%) and agar (0.8%). The cultures were maintained at 25±+2° C. under continuous dark condition. After initiation the callus was maintained on the same medium as well as on medium supplemented with 2,4-D and kinetin of the respective concentrations with sub-culturing at every 4 weeks interval. The calli were harvested at different growth phases and extracted with ethanol (5 g/20 ml). The ethanol extract was concentrated under reduced pressure to a semi-solid residue. The residue was treated with water and extracted with dichloromethane. The dicholoromethane extract was column chromatographed over florosil. The column was first eluted with hexane and then with hexane-chloroform mixtures. The eluant of the latter on concentration gave catechin penta acetate (yield 0.05%).

EXAMPLE 4

Catechin penta acetate (500 mg) was dissolved in 1N methanolic NaOH solution (20 ml) with stirring. It was then diluted with water and extracted with EtoAc (3×50 ml), ethyl acetate layer was washed with water, dried over anhydrous sodium sulfate and concentrated to give (+) catechin (285 mg).

Advantages

1) The above process of the invention provides for the first time a source of catechin penta acetate, a precursor of (+) catechin.
2) Following the process of the present invention (+) catechin penta acetate can be obtained as a single entity in the cell cultures of *Taxus wallichiana* which in turn can be converted into catechin and its other derivatives.
3) The isolation process of catechin penta acetate did not need any extreme condition, thus the process will be practicable.
4) (+) catechin penta acetate is stable towards aerial oxidation and does not polymerize and hence it has a higher self life.

What is claimed is:

1. A process for the production of a compound (+) catechin penta acetate of formula I

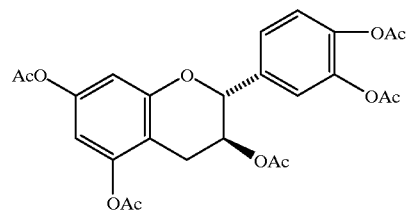

from *Taxus wallichiana* tissue cultures which comprises: (a) inoculation of explants on different media compositions supplemented with combinations of auxins (1–5 mg/l) and cytokinins (0.1–1.0 mg/l); (b) incubation of the cultures under continuous light or dark conditions for 4–6 weeks for callus cultures followed by subculturing at 4–6 week intervals; (c) harvesting the calli at different growth phases ranging from 12–36 months; (d) extracting fresh pulverized calli with polar solvents at room temperature; (e) evaporating the solvent to give a residue and partitioning of the residue between water and chlorinated solvents and evaporating the solvent to a semisolid mass; (f) subjecting the resultant mass to column chromatography over a suitable adsorbent; and (g) eluting with organic solvent/mixtures of organic solvents to get (+) catechin penta acetate.

2. The process as claimed in claim 1, wherein the different explants used to initiate calli may be selected from needles, twigs, stem segments devoid of needles and seeds of *Taxus wallichiana*.

3. The process as claimed in claim 1, wherein the media compositions used may be selected from Murashinge and Skoog (MS), Gamborg (B5), White and Nitsch and Nitsch basal media.

4. The process as claimed in claim 1, wherein the auxin supplements used may be selected from indole acetic acid, napthelene acetic acid, 2,4-dichlorophenoxy acetic acid, 2,4,6-trichlorophenoxy acetic acid, picloram and indole butyric acid.

5. The process as claimed in claim 1, wherein the cytokinin supplements used may be selected from 6-benzyl amino purine, 6-methyl aminopurine, kinetin, zeatin, 2-isopentenyl amino purine, and thiadiazuron.

6. The process as claimed in claim 1, wherein the conditions used to maintain the cultures may be selected between continuous light of 300–3000 lux or dark conditions.

7. The process as claimed in claim 1, wherein the harvesting time may range between twenty four months to thirty six months.

8. The process as claimed in claim 1, wherein the polar solvent used to extract the callus may be selected from methanol, ethanol, propanol, and butanol.

9. The process as claimed in claim 1, wherein the ratio of auxin and cytokinin used ranges between 12 to 20:1.

10. The process as claimed in claim 1, wherein the medium may be supplemented with casein hydrolysate ranging between 100–400 mg/l.

11. The process as claimed in claim 1, wherein the chlorinated solvent used for partitioning may be selected from chloroform and dichloromethane.

12. The process as claimed in claim 1, wherein the adsorbents used for column chromatography for isolating (+) catechin penta acetate may be selected from silica gel, alumina, and florosil.

13. The process as claimed in claim 1, wherein the organic solvent/mixtures of organic solvents used for eluting the column may be selected from ethyl acetate, chloroform, dichloromethane, hexane-ethyl acetate mixtures, Pet. ether-ethyl acetate mixtures, hexane-chloroform mixtures and Pet. Ether-chloroform mixtures.

* * * * *